__United States Patent__ [19]

Vivino

[11] 4,220,653

[45] Sep. 2, 1980

[54] ADMINISTRATION OF CIMETIDINE TO REDUCE APPETITE AND FACILITATE WEIGHT LOSS IN PERSONS SUFFERING FROM EXCESSIVE WEIGHT

[76] Inventor: A. Earl Vivino, Rte. 2, Box 455, Frederick, Md. 21701

[21] Appl. No.: 6,171

[22] Filed: Jan. 24, 1979

[51] Int. Cl.$^2$ ............................................ A61K 31/415
[52] U.S. Cl. ................................................ 424/273 R
[58] Field of Search ..................................... 424/273 R

[56] References Cited

U.S. PATENT DOCUMENTS

| | | | |
|---|---|---|---|
| 3,894,444 | 7/1975 | Durant et al. | 424/273 R |
| 3,950,333 | 4/1976 | Durant et al. | 424/273 R |
| 4,000,302 | 12/1976 | Black et al. | 424/269 |
| 4,112,234 | 9/1978 | Crenshaw et al. | 424/273 R |

*Primary Examiner*—Douglas W. Robinson
*Attorney, Agent, or Firm*—Cushman, Darby & Cushman

[57] ABSTRACT

[N''-cyano-N-methyl-N'[2[[(5methyl-1H imidazol-4-yl)methyl]thio]ethyl]guanidine (known as cimetidine) is administered to persons suffering from excessive weight. Preferably a 300 mg. dose is administered orally with each meal. The treatment reduces the feeling of hunger and therefore assists said persons in reducing their intake of food.

5 Claims, No Drawings

ADMINISTRATION OF CIMETIDINE TO REDUCE APPETITE AND FACILITATE WEIGHT LOSS IN PERSONS SUFFERING FROM EXCESSIVE WEIGHT

BRIEF SUMMARY OF THE INVENTION

The present invention relates to a treatment to assist persons in reducing weight, more specifically by reducing appetite.

BACKGROUND OF THE INVENTION

Excessive weight is a common problem of persons living in advanced civilizations. It is an illness in its own right and has been associated with heart attack, high blood pressure, stroke, and kidney and metabolic disorders. The causes of excessive weight include the greater availability of food, dietary preference for fatty meat and reduction in physical activity associated with advanced civilizations.

Increases in physical activity can help to reduce weight. However, only moderate weight losses can be achieved by overweight persons through reasonable amounts of physical activity. Therefore weight loss ordinarily requires reducing the amount of food consumed.

It might seem simple for persons to eat less food. However, social and psychological factors increase appetite, and most persons find it very difficult to achieve the self-control needed to reduce food intake sufficiently for even gradual weight losses. Various fad diets have been advocated from time-to-time to achieve rapid weight loss during short periods of time, but persons who use such diets usually regain the lost weight quickly. In addition, various drugs have been promoted to help persons reduce appetite, especially certain amphetamines, which may be habit-forming and have dangerous side effects.

SUMMARY OF THE INVENTION

The present invention has as its object the administration to overweight persons of a pharmaceutical composition which reduces appetite but is not dangerous or habit-forming. The composition administered is a histamine $H_2$ receptor antagonist which suppresses gastric secretions. In accordance with the present invention, said composition has been found to suppress appetite in overweight persons.

DETAILED DESCRIPTION OF PREFERRED EMBODIMENTS

The histamine $H_2$ receptor antagonist utilized in accordance with the present invention is cimetidine, whose chemical name is [N"-cyano-N-methyl-N'[2[[(5 methyl-1H imidazol-4-yl)methyl]thio]ethyl]guanidine, whose structural formula is:

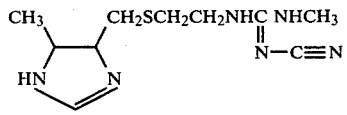

This active agent may be administered orally in tablets which may contain a pharmaceutically acceptable carrier, or by intramuscular injection, in which case cimetidine is utilized as its hydrochloride. It reduces secretion of gastric juices, including pepsin and gastric acids, which ordinarily is stimulated by food and also by psychological and social factors. It is believed that these secretions create a feeling which overweight persons associate with hunger, causing them to eat more food than they require. By reducing these secretions, such persons have less desire to overeat, and therefore reduce their consumption of food.

A preferred mode of administration involves administering cimetidine orally with each meal, preferably after food has been consumed, and more especially at the completion of the meal. The dosage should be sufficient to reduce gastric secretion, and preferably each dose, i.e., at each meal, is 300 mg. This dosage promptly suppresses further gastric secretions. It also reduces a feeling of hunger which overweight persons experience when they consume smaller meals than those to which they have been accustomed. This dosage suppresses gastric secretion for several hours, and reduces the desire for between-meal snacks. However, if any food is consumed between regular meals, a further 300 mg. dose preferably is administered, as if a regular meal had been consumed. In addition, a 300 mg. dose is recommended at bedtime. Preferably the total dosage does not exceed 2,400 mg. daily.

For present purposes, overweight persons are defined as persons whose weight exceeds the weight given in the following chart which is derived from the pamphlet "Calories and Weight" published by the United States Department of Agriculture Home Garden Bulletin No. 153. In this chart, persons with small frames should maintain a weight at the lower end of the stated range and persons with a large frame should maintain a weight near the higher end of the range:

| Desirable Weight Ranges for Adults | | |
|---|---|---|
| | Height (without shoes) Inches | Weight (without clothes) Pounds |
| Men: | 64 | 122–144 |
| | 66 | 130–154 |
| | 68 | 137–165 |
| | 70 | 145–173 |
| | 72 | 152–182 |
| | 74 | 160–190 |
| Women: | 60 | 100–118 |
| | 62 | 106–124 |
| | 64 | 112–132 |
| | 66 | 119–139 |
| | 68 | 126–146 |
| | 70 | 133–155 |

A more precise definition of excess weight is based on body fat content. A person's proportion of body fat can be determined by gravity or skin caliper measurements. Such measurements are described in the popular text, "The Aerobics Way" by Kenneth Cooper (1977) which describes procedures for measurements and cites sources of more information. That text indicates that acceptable levels are less than 19% for men and less than 22% for women.

Persons whose weight is excessive preferably should reduce their daily consumption of food by 500–1,000 calories per day, which will induce a weight loss of 1–2 pounds per week. If a person's normal diet is causing weight gain, the consumption of food whould be reduced further to sustain such a weight loss. The treatment in accordance with the present invention assists a person to reduce food intake by these amounts. Regular exercises should also be undertaken, if the person's health will permit it.

Continuation of the treatment according to the present invention tends to suppress the feeling of hunger which overweight persons experience in certain social situations and therefore assists such persons in developing more satisfactory eating habits on a permanent basis. Cimetidine has previously been used for treatment of duodenal ulcer (up to 8 weeks) and pathological hypersecretory conditions (i.e., Zollinger-Ellison) syndrome, systemic mastocytosis, multiple endocrine adenomas). However, its use in accordance with the present invention is not limited to persons who exhibit these conditions.

The method according to the invention has been evaluated in forty-two cases which are summarized in the following table:

1. Ages range 30-55 years old—half males and half females.
2. All had slightly elevated blood cholesterol
3. All had a blood pressure of 150/90 or slightly higher.
4. All had hunger cramps mid-morning, mid-afternoon and evening.
5. All had taken antacids with relief or ate food for relief; everyone ate food for relief of epigastric cramps.
6. Upper G.I. X-rays were negative for active duodenal ulcer, but either showed some duodenal spasm or the X-rays were negative.
7. All were essentially in normal health, as determined by examination and other laboratory studies.
8. All patients were told to eat three meals per day up to the point of satisfying hunger, and not to eat beyond this point.
9. All were given cimetidne 300 mg. tablets immediately after each meal and at bed time. They were instructed that, if they were not hungry, to eat small amounts of each balanced food. All were told to drink 5-6 glasses of water per day and to select food which was low in fat and salt. They were told that if they had coffee or tea in mid-morning or mid-afternoon, to take 300 mg. of cimetidine after the drink.
10. All patients lost between 1-2 pounds per week. After they reached their normal weights, they continued the cimetidine treatment for two weeks and then tapered down to zero drug treatment. They remained on the sensible diet to maintain their weight with no epigastric pains.
11. No side effects were noted; patients felt very good, and have maintained the best weight they had, comparable to that in high school or college, or better.
12. After a couple of days on this method of weight reduction, many patients were able to thrive all day without food or perhaps only eating some fruit or a salad, without feeling hungry.
13. It also was discovered that a patient could go home from a full day's work, and not be hungry; but, it is human nature, that if persons are exposed to food they would eat. During the day, with no exposure to food, they were not hungry.
14. In all cases the cholesterol and blood pressure returned to normal.
15. No patient was on any other medication.

It will be understood that only preferred embodiments have been described. However, as will be evident, changes may be made, e.g., in composition and dosage, without departing from the scope of the invention, as defined in the following claims.

What is claimed is:

1. A method of reducing the appetite of a person suffering from excessive weight which comprises orally administering to said persons an appetite reducing amount of cimetidine which is effective to reduce gastric secretion.

2. A method as set forth in claim 1 in which cimetidine is administered orally with a meal.

3. A method as set forth in claim 2 in which cimetidine is administered orally with a meal, after at least some food has been consumed.

4. A method as set forth in claim 3 in which cimetidine is administered orally at the completion of a meal.

5. A method as set forth in claim 2 in which a 300 mg. dose of cimetidine is administered orally with each meal.

* * * * *